United States Patent
Tsuji et al.

(10) Patent No.: US 7,053,226 B2
(45) Date of Patent: May 30, 2006

(54) PROCESS FOR PRODUCING CUMENE

(75) Inventors: Junpei Tsuji, Ichihara (JP); Noriaki Oku, Ichihara (JP)

(73) Assignee: Sumitomo Chemical Company, Limited, Osaka (JP)

( * ) Notice: Subject to any disclaimer, the term of this patent is extended or adjusted under 35 U.S.C. 154(b) by 195 days.

(21) Appl. No.: 10/489,241

(22) PCT Filed: Sep. 10, 2002

(86) PCT No.: PCT/JP02/09213

§ 371 (c)(1),
(2), (4) Date: Mar. 11, 2004

(87) PCT Pub. No.: WO03/024901

PCT Pub. Date: Mar. 27, 2003

(65) Prior Publication Data

US 2004/0210068 A1    Oct. 21, 2004

(30) Foreign Application Priority Data

Sep. 13, 2001    (JP)    ............................. 2001-277700

(51) Int. Cl.
*C07D 301/19*    (2006.01)
*C07C 1/22*    (2006.01)
*C07C 1/24*    (2006.01)

(52) U.S. Cl. ...................................... 549/529; 585/469
(58) Field of Classification Search ................ 549/529; 585/469

See application file for complete search history.

(56) References Cited

U.S. PATENT DOCUMENTS

| 3,337,646 A | * | 8/1967 | Khoobiar .................... 585/469 |
| 6,410,806 B1 | | 6/2002 | Oku et al. |
| 6,639,086 B1 | | 10/2003 | Tsuji et al. |
| 6,646,139 B1 | | 11/2003 | Seo et al. |

FOREIGN PATENT DOCUMENTS

| JP | 2001-270880 A | 10/2001 |
| WO | WO 01/70711 A1 | 9/2001 |
| WO | WO 01/70714 A1 | 9/2001 |

* cited by examiner

*Primary Examiner*—Bernard Dentz
(74) *Attorney, Agent, or Firm*—Sughrue Mion, PLLC

(57) ABSTRACT

A process for producing cumene, characterized by preparing a copper-based catalyst by reducing a copper-based catalyst precursor containing copper in an oxidized state with hydrogen in liquid cumene, and subjecting cumyl alcohol to hydrogenolysis in the presence of the copper-based catalyst, and a process for producing propylene oxide which includes that process.

3 Claims, No Drawings

PROCESS FOR PRODUCING CUMENE

This application is the national stage of PCT/JP02/09213 filed Sep. 10, 2002.

TECHNICAL FIELD

The present invention relates to a process for producing cumene. More particularly, the present invention relates to a process for producing cumene having excellent characteristics that a catalyst in the original oxidized state can be reduced economically while preventing the catalyst from deteriorating by heat, and further that a washing step of the catalyst is not newly required at use of the catalyst.

BACKGROUND ART

Cumyl alcohol is converted into cumene through hydrogenolysis in the presence of a copper-based catalyst. Herein, the copper-based catalyst is usually provided as a precursor in which copper contained therein is in an oxidized state, therefore, it requires a reduction by hydrogen in use. However, there is a problem that the reduction generates heat, the heat is accumulated in the catalyst thereby to cause sintering thereof and the like, and the catalyst is deteriorated. For avoiding the problem, there is a method of diluting hydrogen with a large amount of nitrogen to proceed the reduction mildly. However, there is a problem that this method requires a large amount of nitrogen, therefore, is not economical.

DISCLOSURE OF THE INVENTION

Under such situations, an object of the present invention is to provide a process for producing cumene having excellent characteristics that a catalyst in an original oxidation state can be reduced economically while preventing the catalyst from deteriorating by heat, and further that a washing step of the catalyst is not newly required at use of the catalyst.

Namely, the present invention relates to a process for producing cumene, which comprises preparing a copper-based catalyst by reducing a copper-based catalyst precursor containing copper in an oxidized state with hydrogen in liquid cumene, and subjecting cumyl alcohol to hydrogenolysis in the presence of the copper-based catalyst.

BEST MODE FOR CARRYING OUT THE INVENTION

As the copper-based catalyst used for producing cumene by subjecting cumyl alcohol to hydrogenolysis, copper, Raney copper, copper-chromium, copper-zinc copper-chromium-zinc, copper-silica, copper-alumina and a compound containing these are illustrated.

Since the copper-based catalyst is provided as a catalyst precursor in which copper is oxidized, it is necessary to convert the precursor into the catalyst through reduction of the precursor prior to use. In the present invention, the precursor is reduced by hydrogen in a liquid containing cumene.

As conditions of the reduction, the hydrogen concentration in cumene is preferably 0.01 to 1.0% by weight, more preferably 0.01 to 0.1 by weight, a LHSV (Liquid Hourly Space Velocity) of cumene is preferably 0 to 10 h$^{-1}$ (herein, when LHSV is 0, it means a batch method), and the reduction temperature is preferably 100 to 250° C., more preferably 140 to 200° C. Further, it is preferable to control so that the difference between a temperature of an inlet and that of a hot spot becomes 30° C. or less for preventing from sintering of the catalyst during reduction.

In the present invention, as a method of producing cumene by subjecting cumyl alcohol to hydrogenolysis in the presence of the copper-based catalyst, the following manners are illustrated. The hydrogenolysis is usually carried out by contacting cumyl alcohol with hydrogen in the presence of the catalyst. The reaction can be carried out in a liquid phase using a solvent or in a gas phase. The solvent should be substantially inert to the reactants and the product. The solvent may be composed of a substance existing in a cumyl alcohol solution used. When, for example, cumyl alcohol is a mixture with cumene as the product, it is possible to use cumene as a substitute for the solvent without adding a solvent in particular. Other useful solvents include alkanes (e.g. octane, decane, dodecane) and aromatic monocyclic compounds (e.g. benzene, ethylbenzene, toluene) and the like.

The hydrogenolysis temperature is usually 0 to 500° C., and preferably 30 to 400° C. The pressure is advantageously 100 to 10000 kPa. The hydrogenolysis can be advantageously carried out using the catalyst in the form of a slurry or a fixed-bed.

The process of the present invention can be carried out by a batch process, a semi-continuous process, or a continuous process.

Further, the process of the present invention is favorably applied to a hydrogenolysis step in production of propylene oxide containing the following steps:

oxidation step: a step of obtaining cumene hydroperoxide by oxidizing cumene;

epoxidation step: a step of obtaining propylene oxide and cumyl alcohol by reacting cumene hydroperoxide obtained in the oxidation step with propylene in an excess amount in the presence of an epoxidation catalyst in a liquid phase; and hydrogenolysis step: a step of obtaining cumene by subjecting cumyl alcohol obtained in the epoxidation step to hydrogenolysis, and recycling the cumene to the oxidation step as a raw material for the oxidation step.

The oxidation step is a step for obtaining cumene hydroperoxide by oxidizing cumene. The oxidation of cumene is usually effected by autoxidation with oxygen-containing gas such as the air, an oxygen-concentrated air or the like. The oxidation may be carried out without any additive or using an additive such as an alkali. The reaction temperature is usually 50 to 200° C., and the reaction pressure is usually between the atmospheric pressure and 5 MPa. In the oxidation method using the additive, the alkali reagent used includes alkali metal compounds such as NaOH and KOH, alkaline earth metal compounds, alkali metal carbonates such as $Na_2CO_3$ and $NaHCO_3$, ammonia, $(NH_4)_2CO_3$, alkali metal ammonium carbonates and the like.

The epoxidation step is a step for obtaining propylene oxide and cumyl alcohol by reacting cumene hydroperoxide with propylene in an excess amount in the presence of an epoxidation catalyst in a liquid phase.

As the epoxidation catalyst, from a viewpoint of obtaining the target product in high yield and under high selectivity, a solid catalyst containing a titanium-containing silicon oxide is preferable. The catalyst is preferably a so-called titanium-silica catalyst containing titanium chemically bound to silicon oxide. Examples thereof can include substances carrying a titanium compound on a silica carrier, substances in which a titanium compound is compounded with a silicon oxide by a co-precipitation or sol-gel method, and titanium-containing zeolite compounds.

Cumene hydroperoxide used as a raw material for the epoxidation step may be a dilute or thick purification or non-purification product.

The epoxidation is carried out by contacting propylene and cumene hydroperoxide with the catalyst. The reaction is conducted in a liquid phase using a solvent. The solvent should be a liquid under the reaction temperature and pressure, and substantially inert to the reactants and the product. The solvent may be composed of a substance existing in a solution of the hydroperoxide used. When, for example, cumene hydroperoxide is a mixture with cumene as the raw material, it is also possible to substitute cumene for a solvent, without adding a solvent in particular. Other useful solvents include aromatic monocyclic compounds (e.g. benzene, toluene, chlorobenzene, o-dichlorobenzene), alkanes (e.g. octane, decane, dodecane) and the like.

The epoxidation temperature is generally 0 to 200° C. and preferably 25 to 200° C. The pressure may be any pressure sufficient to keep a liquid state of the reaction mixture. Generally, the pressure is advantageously 100 to 10000 kPa.

The epoxidation catalyst can be advantageously used in the form of a slurry or a fixed-bed. The fixed-bed is preferred in the case of a large-scale industrial operation. In addition, the reaction can be carried out by a batch process, a semi-continuous process, a continuous process or the like. When a liquid containing the raw materials for reaction is passed through a fixed-bed, the catalyst is not contained at all or substantially in a liquid mixture discharged from a reaction zone.

The molar ratio of propylene to cumene hydroperoxide supplied to the epoxidation step, is preferably 2/1 to 50/1. When the ratio is less than 2/1, the efficiency may be deteriorated because of decrease of the reaction rate. On the other hand, when the ratio is more than 50/1, there is a tendency that energy required in the recovery step becomes large because of increase of a propylene amount to be recycled.

In the hydrogenolysis step, cumene is produced by subjecting cumyl alcohol obtained in the epoxidation step to hydrogenolysis in the presence of the copper-based catalyst obtained by reducing the above-described copper-based catalyst precursor containing copper in an oxidized state with hydrogen in liquid cumene, and the produced cumene is recycled to the oxidation step as a raw material of the above-described oxidation step. Preparation of the copper-based catalyst and hydrolysis of cumyl alcohol are as described above.

EXAMPLE

The present invention is explained in detail by Examples.

Example 1

While passing cumene through a fixed-bed flow reactor in which 40 g of an unreduced copper-chromium catalyst precursor was packed, the pressure and temperature in the reactor were elevated to 1 MPaG and 150° C., respectively. At this time, the flow amount was set to a LHSV of 1.5 $h^{-1}$ and cumene flown from the reactor was used by feeding again to the reactor after separated from water produced by reduction. Hydrogen was flown so that the hydrogen concentration in cumene became 0.01% by weight, and the reactor temperature was elevated to 160° C. The flowing was continued for 16 hours at the same temperature to terminate the reduction. During the reduction, the maximum temperature in the reactor was 161 to 162° C. The XRD of a catalyst obtained was measured, and as the result, the particle diameter of copper was 23 nm in (111) face. After the reduction, the reactor was heated to 220° C. and a cumene solution containing 20% by weight of cumyl alcohol was fed at 0.9 g/minute thereto and hydrogen was fed at 500 Ncc/minute. The reaction liquid after 25 hours from the beginning of the feed, was analyzed, and as the result, the conversion of cumyl alcohol was higher than 99% and the selectivity of cumene was 100%.

Comparative Example 1

While passing nitrogen through a fixed-bed flow reactor in which 40 g of an unreduced copper-chromium catalyst precursor was packed, the reactor were heated to 110° C. At this time, the flow amount of nitrogen was set to the GHSV (Gas Hourly Space Velocity) of 200 $h^{-1}$. Hydrogen was flown so that the hydrogen concentration in nitrogen became 1 to 3% by volume, and the reactor temperature was elevated to 130° C. When the reduction was initiated, a hot spot arose at the inlet place of the catalyst layer and the temperature at the part rose to about 160° C.

The flow of hydrogen was controlled so that the temperature difference ($\Delta T$) between the hot spot place and the reactor does not exceed 30° C., and after the hot spot place was moved from the inlet to outlet of the reactor, the reactor temperature was elevated to 200° C., then maintained at the temperature for 10 hours to terminate the reduction.

The XRD of a catalyst obtained was measured, and as the result, the particle diameter of copper was 20 nm in (111) face. After the reduction, the reactor was heated to 220° C. and a cumene solution containing 20% by weight of cumyl alcohol was fed at 0.9 g/minute and hydrogen was fed at 500 Ncc/minute. A reaction liquid after 50 hours from the beginning of the feed, was analyzed, and as the result, the conversion of cumyl alcohol was higher than 99% and the selectivity of cumene was 100%.

As above, it was shown that the catalyst obtained by the liquid phase reduction had a capability equal to that obtained by the gas phase reduction. Further, a localized heat generation during reduction, which causes to deterioration of the capability of the catalyst, must be controlled within 30° C. in the gas phase reduction, and, on the other hand, in the liquid phase reduction, the management of the temperature is easy because the temperature rising is only about 1 to about 2° C. Moreover, in the gas phase reduction, since the gas phase reduction uses a large amount of nitrogen to reduce a localized heat generation, recycling use of nitrogen is desired. But, because large scaled compressor industrially for recycling becomes necessary for only reduction, it can not say to be economical. On the other hand, in cumene, an addition of a new equipment is unnecessary and recycling is easy because a pump used in the process can be used as it is if a circulating line is installed.

INDUSTRIAL APPLICABILITY

As described above, according to the present invention, a process for producing cumene having excellent characteristics that a catalyst in an original oxidation state can be reduced economically while preventing the catalyst from deteriorating by heat, and further that a washing step of the catalyst is not newly required at use of the catalyst, can be provided.

The invention claimed is:

1. A process for producing cumene, which comprises:
   preparing a copper-based catalyst by reducing a copper-based catalyst precursor containing copper in an oxidized state with hydrogen in liquid cumene, and
   subjecting cumyl alcohol to hydrogenolysis in the presence of the copper-based catalyst.

2. The process according to claim 1, wherein the reduction temperature is 100 to 250° C.

3. A process for propylene oxide, which comprises the following steps:
   oxidation step: a step of obtaining cumene hydroperoxide by oxidizing cumene;
   epoxidation step: a step of obtaining propylene oxide and cumyl alcohol by reacting cumene hydroperoxide obtained in the oxidation step with propylene in an excess amount in the presence of a solid catalyst in a liquid phase; and
   hydrogenolysis step: a step of obtaining cumene by subjecting cumyl alcohol obtained in the epoxidation step to hydrogenolysis in the presence of the copper-based catalyst obtained by reducing a copper-based catalyst precursor containing copper in an oxidized state with hydrogen in liquid cumene, and recycling the cumene to the oxidation step as a raw material for the oxidation step.

* * * * *